Feb. 3 , 1953 E. S. BOERNER Plant Pat. 1,162
CHRYSANTHEMUM PLANT
Filed April 18, 1952
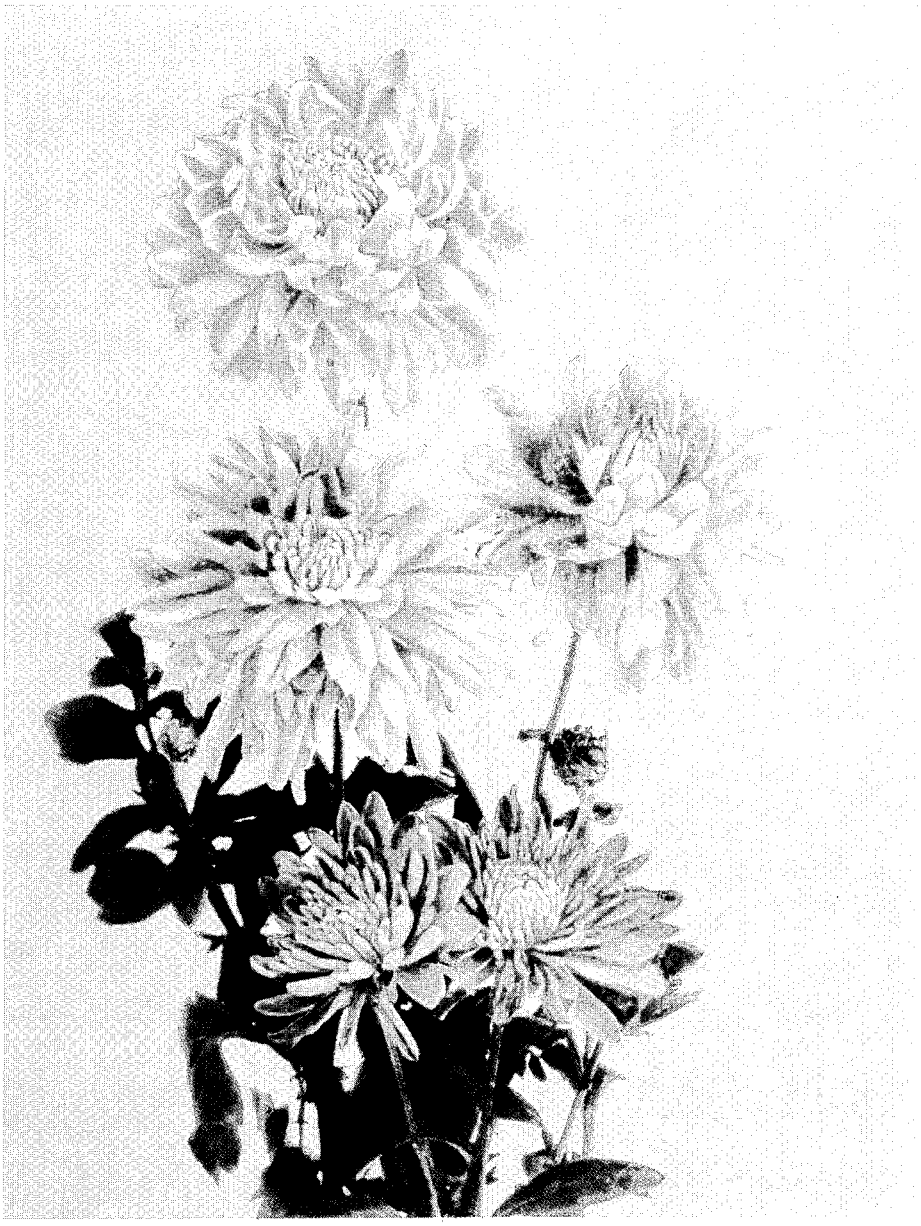
Inventor.
E. S. Boerner
By: Robert Cobb
Attorneys.

Patented Feb. 3, 1953

Plant Pat. 1,162

UNITED STATES PATENT OFFICE 1,162

CHRYSANTHEMUM PLANT

Eugene S. Boerner, Newark, N. Y., assignor to Jackson & Perkins Company, Newark, N. Y., a corporation of New York Application April 18, 1952, Serial No. 283,063

1 Claim. (Cl. 47—60)

The present invention relates to a new and distinct variety of chrysanthemum plant, originated by me by crossing the unpatented variety known as "Burma" with an unnamed and unpatented seedling of the variety known as "September Dawn."

The primary objective in making this cross was to obtain a new variety having the form, growth and other general habits of "September Dawn," in combination with flowers of a color and lasting quality of those of "Burma." This objective was substantially obtained, as evidenced by the fact that the color of the flowers of the new variety is inherited from the parent "Burma" and substantially conforms thereto, while the flowers of the new variety are similar in form to those of the parent seedling of "September Dawn"; the new variety is more bushy than "Burma" and has many more branches; and the new variety shows a greater tendency to "stool" and make runners than the variety "Burma."

In addition to the aforementioned novel features, my new variety is endowed with the following unique combination of characteristics which distinguish the same from its parents, as well as from all other varieties of its class:

(1) There is no other hardy chrysanthemum now in existence having the particular combination of color and shape as that of my new variety, to the best of my knowledge;

(2) The color of the flowers of my new variety is unique in an outdoor chrysanthemum; and (3) The size of the blooms of my variety is quite unusual in chrysanthemums of this general color.

Asexual reproduction of my new variety by top cuttings and also by underground runners, at Newark, New York, shows that the foregoing characteristics come true to form and are established and transmitted through succeeding propagations.

The accompanying drawing shows specimens of the new variety, with the flowers and foliage in different stages of development.

The following is a detailed description of the new variety, as observed in the fields at Newark, New York, in the latter part of the month of September and about at mid-morning, with color terminology in accordance with Ridgway's Color Standards and Nomenclature:

Parentage: "Burma" X an unnamed seedling of "September Dawn."

Classification: Decorative type; outer petals quill backward slightly in the final opening, then remain double in the center throughout; centers are twirled until the petals unfurl and open.

Growth: Medium; 3 ft. to 3½ ft. in height.

Cold resistance: Plant winter hardy in Northern New York; flowers frost resistant.

Blooming period: In Newark, New York, climatic area, date of start of bloom is about the middle of September, and the plant blooms and makes a big show until severe freezing in October and November.

Bud:

*Color.*—When sepals first divide—Acajou Red, Plate 13. When petals begin to unfurl—Eugenia Red, Plate 13. When half blown—inside of petals—English Red, Plate 2; reverse of petals—Light Orange Yellow, Plate 3, lightly overcast with Congo Pink, Plate 28.

*Peduncle.*—Color—Light Cress Green, Plate 31. Strength—strong; erect.

Bloom:

*Size.*—4" to 4½".

*Stem.*—Strong; normal.

*Form.*—Decorative.

*Petalage.*—Double.

*Color.*—Center of flower—Xanthine Orange, Plate 3, lightly overcast with Salmon Orange, Plate 2. Outer petals—Apricot Yellow, Plate 4, lightly overcast with Carrot Red, Plate 14. Base of petals—Buff Yellow, Plate 4, lightly overcast with Carrot Red, Plate 14. Inside of petals—Apricot Yellow, Plate 4, lightly overcast with Rufous, Plate 14. Reverse of petals—Maize Yellow, Plate 4.

*Petals.*—Texture—medium. Form—Oval.

Fragrance: Characteristic chrysanthemum.

Plant:

*Form.*—Upright.

*Growth.*—Free; generous bottom breaks.

Foliage:

*Size.*—Medium.

*Quantity.*—Normal.

*Color.* — Upper side—Dark Cress Green, Plate 31; reverse side—Bice Green, Plate 17.

*Texture.*—Leathery.

I claim:

A new and distinct variety of chrysanthemum plant of the decorative class, substantially as herein shown and described, characterized particularly as to novelty by the unusual combination of color, shape and size of its flowers which is unique in outdoor chrysanthemums, by its bushier habit of growth and its production of many more branches, and by its greater tendency to stool and produce runners.

EUGENE S. BOERNER.

No references cited.